United States Patent [19]

Clough et al.

[11] Patent Number: 4,778,821

[45] Date of Patent: Oct. 18, 1988

[54] METHOD FOR CONTROLLING HELMINTIC PARASITES

[75] Inventors: Ellen R. Clough, Elmhurst, Ill.; Carl K. Edwards, III, Terre Haute, Ind.

[73] Assignee: International Minerals & Chemical Corp., Terre Haute, Ind.

[21] Appl. No.: 73,821

[22] Filed: Jul. 15, 1987

[51] Int. Cl.[4] .......................................... A61K 31/335
[52] U.S. Cl. ................................................... 514/450
[58] Field of Search ......................................... 514/450

[56] References Cited

U.S. PATENT DOCUMENTS

| | | | |
|---|---|---|---|
| 3,239,341 | 3/1966 | Hodge et al. | 514/450 |
| 3,239,345 | 3/1966 | Hodge et al. | 514/450 |
| 3,239,348 | 3/1966 | Hodge et al. | 514/450 |
| 3,239,354 | 3/1966 | Hodge et al. | 514/450 |
| 3,265,580 | 8/1966 | Nelson | 167/74 |
| 3,275,516 | 9/1966 | Eppstein | 167/74 |
| 3,317,292 | 5/1967 | Eppstein | 167/74 |
| 3,453,367 | 7/1969 | Bachman et al. | 514/450 |
| 4,639,435 | 1/1987 | Fujii et al. | 514/11 |
| 4,666,839 | 5/1987 | Souza | 435/91 |

OTHER PUBLICATIONS

Lewis et al., "Human Prolactin: Isolation and Some Properties", Biochemical and Biophysical Research Communications, vol. 44, No. 5, 1971.

Doneen et al., "Studies on Prolactin, Selective Reduction of the Disulfide Bonds of the Ovine Hormone", Biochem., 18,4851–4860(1979).

Primary Examiner—Jerome D. Goldberg
Attorney, Agent, or Firm—Wendell R. Guffey; Thomas L. Farquer

[57] ABSTRACT

A method for controlling helmintic parasites in animals which comprises administering alone or in combination at least one Resorcylic Acid Lactone (RAL) compound selected from the group consisting of zearalenone, zearalanone, zearalene, zearalane, zearalenol, zearalanol, and dideoxyzearalane to the animal. The RAL compounds are administered to animals infected with or susceptible to infection by helmintic parasites to control the parasite population.

14 Claims, No Drawings

METHOD FOR CONTROLLING HELMINTIC PARASITES

This invention relates generally to methods for controlling helmintic parasites and particularly to methods for controlling helmintic parasites using Resorcylic Acid Lactone (RAL) compounds.

BACKGROUND OF THE INVENTION

Diseases caused by helmintic parasite infections far outnumber diseases caused by other infectious agents. It is estimated that one billion people are infected with roundworm alone and that eight hundred million people are infected with hookworm. This does not include infections caused by other helmintic parasites nor include the millions and perhaps billions of animals infected with helmintic parasites. The taxonomic, identification, classification, and history of helmintic parasites and the epidemiology, treatment, and conduct of the more prevalent parasitic infections is reviewed in *Parasitology for Veterinarians* by J. R. Georgi, W. B. Sanders Co., 3rd edition (1980).

Attempts to control helmintic parasites are disclosed in ancient Chinese and Egyptian writings dating back 3500 years. More recently, there has been a continuing effort to develop methods for treating infected animals and controlling the spread of helmintic parasite infections. Broad spectrum anthelmintic agents such as aminoglycoside antibodies, organophosphorous compounds, benzimidazoles, organic arsenic compounds, piparazines, imidoylureas are a few among many anthelmintic agents that have been used to treat and control the spread of helmintic parasite infections. These anthelmintic agents generally function by destroying helmintic parasites in various developmental stages including adults, larvae, and eggs. Many of these compounds, however, are toxic to the host in effective dosages, difficult to prepare or synthesize, expensive, or produce adverse side effects when administered to the host animal. There exists, therefore, a continuing need for new and more effective methods for controlling helmintic parasites.

Previous methods for controlling helmintic parasites include the following: U.S. Pat. Nos. 3,390,148 discloses the use of thioimidates as anthelmintic agents. 3,458,633 discloses the use of thiazoline derivatives as anthelmintic agents. 3,915,986 discloses the use of 5-propylthio-2-benzimidazole carbamate against gastro-intestinal parasites in animals. 3,721,740 discloses the use of phenylhydrazone derivatives as anthelmintic agents. 4,175,135 discloses a method for controlling acarina ectoparasites using 2-aryl-1,3-cyclohexanedione. 4,255,447 discloses the use of phenylcyclopropane carboxycylic acid derivatives having acaracidal properties. 4,299,837 discloses using benzimidazole-carbamates as anthelmintic agents. 4,468,390 discloses anthelmintic compositions comprising antibiotics, benzimidazole, salicylamide, and isoquinoline compounds. 4,105,779 discloses oral anthelmintic compositions comprising phosphate compounds and thermoplastic resins. 4,287,176 discloses using thermally revisable gels containing levamisole, tetramisole, butamisole and benzamisole. 4,348,389 discloses administering substituted quinoxaline adducts to infested animals to control parasitic worms. 4,337,274 discloses flukicidal diphenylether compounds. 4,593,024 to Lu et al. discloses dihydroisoxazole compounds having anthelmintic properties. 4,009,266 discloses a method for controlling gastro-intestinal nematode parasites in domestic animals. 3,978,060 discloses new compounds used to eradicate internal parasites. 3,980,791 discloses pour-on tetramisole and levamisole anthelmintic compositions.

The RAL compounds of the present invention are known compounds. Preparation of the RAL compounds of the present invention, zearalenone, zearalanone, zearalene, zearalane, zearalenol, zearalanol, and dideoxyzearalane, are disclosed in U.S. Pat. Nos. 3,196,019, 3,239,354, 3,239,341, 3,239,348, 3,239,345, and 3,453,367, all incorporated herein by reference. The compounds are used as growth promotants in animals.

SUMMARY OF THE INVENTION

It is, therefore, an object of the present invention to provide a method for treating animals suffering from helmintic parasite infections.

It is another object of the present invention to provide a method for preventing infection by helmintic parasites.

It is a further object of the present invention to provide a composition useful for controlling helmintic parasites.

These and other objects are achieved by administering helmintic parasite controlling amounts of the Resorcylic Acid Lactone (RAL) compounds zearalenone, zearalanone, zearalene, zearalane, zearalenol, zearalanol, and dideoxyzearalane to the animal. The compounds are administered alone or in combination in dosages from about 1-20 mg/kg of body weight during or prior to an anticipated helmintic parasite infection to prevent or treat the disease and the resulting clinical manifestations. Preferably, RAL compounds of the present invention are administered to the animal prior to an anticipated infection to prevent the resulting disease or administered to the animal after the disease occurs to reduce the parasite population.

In the preferred embodiment, zearalane and zearalanol are administered to animals infected by trematodes, cestodes, and nematodes, particularly migratory respiratory and gastro-intestinal parasites, in dosages from about 1-20 mg/kg of body weight to control the parasite population.

According to the present invention, at least one compound selected form the group consisting of zearalenone, zearalanone, zearalene, zearalane, zearalenol, zearalanol, and dideoxyzearalane is admixed with a pharmaceutically acceptable carrier to form a composition useful for controlling helmintic parasites. The composition is administered to animals infected with or susceptible to infection by helmintic parasites to control the parasite population.

Other objects, advantages, and novel features of the present invention will become apparent from the following detailed description of the invention.

DETAILED DESCRIPTION OF THE INVENTION

The following terms used herein are defined as follows: "helmintic parasite" is defined to include parasites in the adult, larvae, and egg stage; and "to control" and "controlling" helmintic parasites are defined to include (1) administering RAL compounds of the present invention to helmintic parasite infected animals to treat the disease by eliminating or reducing the helmintic parasite population, and (2) administering RAL compounds of the present invention to noninfected animals to prevent future infection by helmintic parasites.

The Resorcylic Acid Lactone (RAL) compounds useful in the present invention are the known compounds zearalenone, zearalanone, zearalene, zearalane, zearalenol, zearalanol, and dideoxyzearalane.

Zearalenone is prepared by cultivating the organism *Gibberella zeae* (Gordon) on deposit at the Northern Utilization Research and Development Division of the United States Department of Agriculture under the number NRRL-2830 according to the method disclosed in U.S. Pat. No. 3,196,019, incorporated herein by reference.

Zearalanone is prepared by reducing the macrocylic ring double bond of zearalenone according to the method disclosed in U.S. Pat. No. 3,239,354, incorporated herein by reference.

Zearalene and zearalane are prepared by (1) removing the ring ketone group of zearalenone and (2) reucing the ring double bond of zearalene according to the method disclosed in U.S. Pat. No. 3,239,341, incorporated herein by reference.

Zearalenol is prepared by reducing the zearalenone ring ketone group to form an alcohol according to the method disclosed in U.S. Pat. No. 3,239,348, incorporated herein by reference.

Zearalanol is produced by reducing the zearalenol ring double bond according to the method disclosed in U.S. Pat. No. 3,239,345, incorporated herein by reference.

Dideoxyzearalane is prepared by removing the hydroxyl groups from zearalane according to the method disclosed in U.S. Pat. No. 3,453,367, incorporated herein by reference.

According to the present invention, a method for controlling helmintic parasites in animals comprises administering alone or in combination at least one Resorcylic Acid Lactone compound selected from the group consisting of zearalenone, zearalanone, zearalene, zearalane, zearalenol, zearalanol, and dideoxyzearalane to the animal. Additionally, a composition for controlling helmintic parasites in animals comprises a Resorcylic Acid Lactone compound selected from the group consisting of zearalenone, zearalanone, zearalene, zearalane, zearalenol, zearalanol, and dideoxyzearalane alone or in combination admixed with an inert pharmaceutical carrier. The RAL compounds are administered to animals infected with or susceptible to infection by helmintic parasites to control the parasite population.

The method of the present invention can be used to control a broad range of helmintic parasites including but not limited to trematodes, cestodes, and nematodes, particularly lungworms, roundworms, tapeworms, ringworms, pinworms, and hookworms. In the preferred embodiment, the RAL compounds of the present invention are administered to animals to control respiratory and gastro-intestinal cestodes and nematodes, particularly migratory parasites such as lungworms, roundworms and tapeworms.

Any animal species susceptible to infection by helmintic parasite can be administered RAL compounds according to the present invention. Human, bovine, porcine, canine, feline, equine, avian, and ovine are preferred, with livestock and poultry such as cattle, swine, sheep, chickens, and turkeys being most preferred.

Although the amount of RAL compounds administered to the animals according to the present infinitive can vary depending on the type of animal, type of infection, degree of infection, and the like, typical dosages administered to the animal range from about 1-20 mg/kg of body weight. Preferably, animals infected with helmintic parasites are administered from about 1-20 mg/kg of body weight. Animals susceptible to infection by helmintic parasites are administered from about 1-10 mg/kg of body weight.

The RAL compounds according to the present invention can be administered to the animals in any acceptable manner including orally, by injection, using an implant, and the like. Injections and implants are preferred because they permit precise control of the timing and dosage levels used for administration. The RAL compounds according to the present invention are preferably administered parenterally. As used herein, parenteral administration means administration by intravenous, intramuscular, subcutaneous, or intraperitoneal injection, or by subcutaneous implant.

The RAL compounds according to the present invention can be administered orally to the animal. Oral administration includes administering the RAL compounds in tablets, suspensions, implants, solutions, boluses, emulsions, capsules, powders, syrups, water compositions, feed compositions, and the like. For example, the RAL compounds can be blended with ordinary feed compositions or added to drinking water in amounts sufficient to treat or prevent helmintic parasite infections.

When the RAL compounds are to be administered in feeds, an animal feed composition may be prepared containing the usual nutritionally-balanced feed containing quantities of carbohydrates, proteins, vitamins and minerals, together with the RAL compounds in accordance with the present invention. Some of the usual dietary elements included in animal feed compositions are grains, such as ground grain and grain by-products, animal protein substances, such as those found in fish meal and meat scraps, vegetable proteins, like soybean oil meal or peanut oil meal; vitamins and vitamin-containing materials, e.g., vitamin A and D mixtures, riboflavin supplements and other vitamin B complex members; and bone meal and limestone to provide minerals. A type of conventional feed material for use with cattle includes alfalfa hay and ground corncobs together with supplementary vitamins and vitamin-containing substances if desired. Similarly, a medicated animal feed composition based on liver meal, such as disclosed in U.S. Pat. No. 4,283,400, incorporated herein by reference, can be used to administer the compounds of the present invention.

The RAL compounds according to the present invention are admixed with the feed in amounts sufficient to supply from about 1-20 mg/kg of body weight, typically 10-100 grams/ton of feed, to the animal.

The RAL compounds according to the present invention can be administered to the animals in an injectable formulation containing any biocompatible and RAL compounds compatible carrier such as various vehicles, adjuvants, additives, and diluents. Such formulations and carriers are well known in the art. The RAL compounds are added to the carrier in amounts sufficient to supply from about 1-20 mg/animal to the animals when injected.

Aqueous vehicles such as water having no nonvolatile pyrogens, sterile water, and bacteriostatic water are also suitable to form injectable RAL compound formulations. In addition to these forms of water, several other aqueous vehicles can be used. These include isotonic injection compositions that can be sterilized such as sodium chloride, carboxymethylcellulose (CMC), Ringer's, dextrose, dextrose and sodium chloride, and lactated Ringer's. Addition of water-miscible solvents, such as methanol, ethanol, or propylene glycol generally increases solubility and stability of the RAL compounds in these vehicles.

Nonaqueous vehicles such as cottonseed oil, sesame oil, or peanut oil and esters such as isopropyl myristate may also be used as solvent systems for the RAL compounds compositions. Additionally various additives which enhance the stability, sterility, and isotonicity of the composition including antimicrobial preservatives, antioxidants, chelating agents, and buffers can be added. Any vehicle, diluent, or additive used would, however, have to be compatible with the RAL compounds according to the present invention. Preferably, the RAL compounds are administered in a squalene, HBSS, or CMC vehicle.

The RAL compounds according to the present invention can be administered to the animals in the form of a slow-release subcutaneous implant which is inserted beneath the skin of the animals. The implant can take the form of a pellet which slowly dissolves after being implanted in the animals or a biocompatible and RAL compound compatible delivery module well known to those skilled in the art. Such well known dosage forms are designed such that the active ingredients are slowly released over a period of several days to several weeks.

The implant according to the present invention, is designed to deliver the RAL compounds in amounts from about 1–50 mg/animal/day, preferably from about 20–25 mg/animal/day.

The invention having been generally described, the following examples are given as particular embodiments of the invention and to demonstrate the practice and advantages thereof. It is understood that the examples are given by way of illustration and are not intended to limit the specification or the claims to follow in any manner.

EXAMPLE 1

The anthelmintic activity of zearalane was evaluated against the parasitic nematode, *Nippostrongylus brasiliensis*, in experimentally infected $CF_1$ male mice. Sixty (60) mice, 4–6 weeks of age weighing approximately 18–20 grams each, were acclimated to new cages and fed pelleted rodent chow (Purina #5002) and water *ad libitum*. The mice were divided into 12 treatment groups; each treatment group consisted of 5 mice per cage with no replicates. Each treatment group was administered zearalane in various vehicles or a control as follows:

| Group | Treatment | Vehicle |
|---|---|---|
| 1 | 1000 μg Zearalane | 1% squalene |
| 2 | 750 μg Zearalane | 1% squalene |
| 3 | 500 μg Zearalane | 1% squalene |
| 4 | 250 μg Zearalane | 1% squalene |
| 5 | 100 μg Zearalane | 1% squalene |
| 6 | 500 μg Zearalane | HBSS |
| 7 | 1% squalene | HBSS |
| 8 | Levamisole | |
| 9 | Non-treated infected | |
| 10 | 1000 μg Zearalane | 1% squalene with 2% CMC |
| 11 | 100 μg Zearalane | 1% squalene with 2% CMC |
| 12 | 1% squalene | 2% CMC |

The zearalane compositions and controls were administered via subcutaneous injection. Groups 1–5 were treated with an emulsion of the experimental compound in 1% squalene. Group 6 was treated with Zearalane in HBSS (Hank's Balanced Salt Solution) while Group 7 was treated with an emulsion of 1% squalene in HBSS Levamisole (Cyanide), a commercial anthelmintic product, was administered at a dosage of 9.6 μg/mouse and served as a positive control. Group 9 served as the negative control with infections with the parasite but no treatments administered. Groups 10 and 11 were treated with an emulsion of Zearalane in 1% squalene combined with 2% CMC. Group 12 was treated with 1% squalene and 2% CMC for comparisons with Group 10 and 11.

Twenty-four (24) hours after treatments were administered, individual mice were injected subcutaneously with a single dose (0.1 ml) of the infective stage *Nippostrongylus brasiliensis* larvae (approximately 300 L3 forms per injection). The actual number of larvae were counted prior to injection.

The mice were continued on water and feed for the next seven days and were observed for any changes in physical well being.

On the seventh day after injection, the mice were taken off feed in the evening and fasted overnight. The mice were sacrificed the next day and the small intestine of each mouse removed. The small intestine was compressed between two heavy glass plates and the red, adult worms counted. To determine efficacy, the number of worms recovered in drug treated mice were compared with those of non-medicated control mice. The results are shown in Table 1.

Referring to Table 1, mice injected subcutaneously (s.c.) with either 100 μg, 250 μg, 500 μg, or 1000 μg per mouse Zearalane in the squalene vehicle were protected in a dose-related fashion against the migrating larvae through the lungs. There was minimal protection with the vehicle alone (14.9% efficacy). When Zearalane was injected in either a HBSS vehicle (without oil) or a carboxymethylcellulose/1% squalene vehicle (CMC/1%), the protection did not change significantly from the HBSS/1% squalene vehicle. These vehicles also showed low protection alone.

EXAMPLE 2

The anthelmintic activity of zearalane was evaluated against the parasitic nematode, *Nippostrongylus brasiliensis*, in experimentally infected $CF_1$ male mice. Eighty six (86) mice, 4–6 weeks of age weighing approximately 18–20 grams each, were acclimated to new cages and fed pelleted rodent chow (Purina #5002) and water *ad libitum*. The mice were divided into 20 treatment groups; each treatment group consisted of 3 or 5 mice per cage with no replicates. One half of the treatment groups were administered zearalane in various vehicles or a control. To determine if Zearalane is toxic for the larvae, the number of larvae equivalent to one infective dose (300) were allowed to stand in petri dishes containing the treatments, as shown below, for 4 hours. The L3 larvae were aspirated into a tuberculin syringe and injected into the mice in the other treatment groups as follows:

| Group | Treatment | Vehicle |
|---|---|---|
| 1 | 1000 μg Zearalane | 1% squalene in saline |
| 2 | 750 μg Zearalane | 1% squalene in saline |
| 3 | 500 μg Zearalane | 1% squalene in saline |
| 4 | 250 μg Zearalane | 1% squalene in saline |
| 5 | 100 μg Zearalane | 1% squalene in saline |
| 6 | 500 μg Zearalane | HBSS |
| 7 | 0 μg Zearalane | 1% squalene in saline |
| 8 | 12 μg Levamisole | HBSS |
| 9 | 0 μg Zearalane | HBSS |
| 10 | 1000 μg Dideoxyzearalane | HBSS |
| 11 | HBSS (1 ml/dish) | — |
| 12 | N. brasiliensis (injected directly into mice) | — |
| 13 | 1% squalene | saline (1 ml/dish) |
| 14 | Levamisole (12 μg/ml) | |
| 15 | 4000 μg/ml Zearalane | HBSS |
| 16 | 2000 μg/ml Zearalane | HBSS |
| 17 | 400 μg/ml Zearalane | HBSS |
| 18 | 400 μg/ml Zearalane | 1% squalene |
| 19 | 40 μg/ml Zearalane | HBSS |
| 20 | 1000 μg/ml Dideoxyzearalane | HBSS |

Twenty-four (24) hours before treatments were administered, individual mice were injected subcutaneously with a single dose (0.1 ml) of the infective stage *Nippostrongylus brasiliensis* larvae (approximately 300 L3 forms per injection). The actual number of lavvae were counted prior to injection.

The mice were continued on water and feed for the next seven days and were observed for any changes in physical well being.

On the seventh day after infection, the mice were taken off feed in the evening and fasted overnight. The following day the mice were sacrificed and the small intestine of each mouse was removed. The small intestine was compressed between two heavy glass plates and the red, adult worms counted. To determine efficacy, the number of worms recovered in drug-treated mice were compared with those in non-medicated control mice. The results are shown in Table 2.

Referring to Table 2, the data shows a dose-dependent reduction of adult, mature worms in the gut of mice previously treated in vivo with Zearalane. The mice treated with 1000 μg Zearalane showed the greatest reduction. The range of efficacy was found to be 36.1% to 75.4%. The vehicle, either 1% squalene/HBSS alone, had no effect on Zearalane efficacy, since similar effects were seen with either vehicle in mice treated with 500 μg Zearalane. Dideoxyzearalane which has been shown to have a reduced ability to activate peritoneal and alveolar mouse MΦ in vivo and in vitro, was much less active in reducing the adult worms (16.9% efficacy) in the gut.

Referring again to Table 2, the in vitro data shows that anthelmintic activity of Zearalane is related to dosage level. The range of efficacy was found to be 40.7% to 69.2%. Much higher dose levels of these compounds are required to obtain activity similar to that observed in vivo. 4-Deoxy-Zearalanol, a ring-opened RAL with increased lipophilicity, had little (44.7%) in vitro activity.

The data in Table 2 shows that Zearalane, when given at the appropriate dose and route, has potential anthelmintic activity. Although the exact mechanism of how Zearalane may be working remains to be elucidated, it is clear that this compound, delivered s.c. at dosages ranging from 100 μg/mouse to 1000 μg/mouse, reduces adult worm burdens in mice infected with N. brasiliensis. The data also show that Zearalane is active regardless of the vehicle into which it is suspended.

EXAMPLE 3

The anthelmintic activity of zearalane was evaluated against the parasitic nematode, *Nippostrongylus brasiliensis*, in experimentally infected $CF_1$ male mice. One hundred fifty (150) mice, 4–6 weeks of age weighing approximately 18–20 grams each, were acclimated to new cages and fed pelleted rodent chow (Purina #5002) and water *ad libitum*. The mice were divided into treatment groups; each treatment group consisted of 5 mice per cage with no replicates. Each treatment group was administered zearalane in various vehicles or a control as follows:

| Groups | Treatment | Route | Vehicle |
|---|---|---|---|
| 1, 4, 7, 10 13, and 16 | HBSS | s.c. | HBSS |
| 2, 5, 8, 11, 14, and 17 | Levamisole 12 μg/mouse | s.c. | HBSS |
| 3, 6, 9, 12, 15, and 18 | Zearalane 500 μg/mouse | s.c. | HBSS |

Treatments were given on days −6, −3, −1, +1, +3, or +6 before or after subcutaneous infection with *Nippostrongylus brasiliensis* L3 infective larvae. On day 0, all mice were injected subcutaneously with a single dose (0.1 ml) containing approximately 300 infective stage larvae.

The mice were continued on water and feed for the next seven days and were observed for any changes in physical well being.

On the seventh day after infection, the mice were taken off feed in the evening and fasted overnight. The following day the mice were sacrificed and the small intestine of each mouse removed. The small intestine was compressed between two heavy glass plates and the red, adult worms counted. To determine efficacy, the number of worms recovered in drug-treated mice were compared with those in non-medicated control mice. The results are shown in Table 3.

Referring to Table 3, the highest anthelmintic activity (500 μg/mouse/one day; s.c.) was day +1 at 48.8%; Levamisole (positive control 12.0 μg/mouse/one day; s.c.) was day +3 at 82.3%. However, activity was observed throughout the experiment, particularly on days −1 through +5.

EXAMPLE 4

Alveolar MΦ from mice from the above five treatments on day −1 were recovered. After overnight culture, they were incubated with approximately 500 larvae. Using the Nikon Diaphot phase contrast microscope, the appaarance of the larvae settling on the MΦ in vitro was followed during a six hour period. The appearance of these in vivo activated MΦ show that MΦ taken from Zearalane treated (500 μg) mice appear to be more spread out on the dish with numerous pseudopodia extendig from the body of the cells in comparison to the rounded up appearance of the MΦ taken from HBSS treated mice. These are characteristics of activated MΦ.

Approximately 20 minutes after exposure of the nematodes to macrophage from zearalane treated mice, the worms began to curl very tightly and make rapid back and further beating motions. This activity stopped approximately 4 hours after the initiation of the in vitro incubation. Curling and rapid movements were not observed when worms were incubated with macrophage from mice treated with HBSS.

Obviously many modifications and variations of the present invention are possible in light of the above teachings. It is therefore to be understood that within the scope of the appended claims the invention may be practiced otherwise than as specifically described.

TABLE 1

Anthelmintic Activity of Zearalane Against
Nippostrongylus brasiliensis in Mice

| | Treatment | Vehicle | Worm Count Mean | Percent Efficacy |
|---|---|---|---|---|
| 1. | Non-treated Infected | Saline | 214 | — |
| 2. | RAL Zearalane; 1000 μg | HBSS/1% Squalene | 54 | 74.8 |
| 3. | RAL Zearalane; 750 μg | HBSS/1% Squalene | 78 | 63.4 |
| 4. | RAL Zearalane; 500 μg | HBSS/1% Squalene | 107 | 50.1 |
| 5. | RAL Zearalane; 250 μg | HBSS/1% Squalene | 146 | 31.5 |
| 6. | RAL Zearalane; 100 μg | HBSS/1% Squalene | 167 | 21.9 |
| 7. | RAL Zearalane; 500 μg | HBSS | 100 | 53.1 |
| 8. | — | HBSS/1% Squalene | 182 | 14.9 |
| 9. | Levamisole; 96 μg | HBSS | 60 | 71.9 |
| 10. | RAL Zearalane; 1000 μg | 2% CMC/1% Squalene | 55 | 74.2 |
| 11. | RAL Zearalane; 100 μg | 2% CMC/1% Squalene | 158 | 26.1 |
| 12. | — | 2% CMC/1% Squalene | 180 | 15.6 |

*All treatments injected subcutaneously.
HBSS = Hanks Balanced Salt Solution (M.A. Bioproducts)
CMC = Carboxymethylcellulose

TABLE 2

Efficacy Study of Anthelmintic Compounds vs.
Nippostrongylus brasiliensis in Mice

| Treatment | Mean # of Nematodes | Percent Efficacy |
|---|---|---|
| IN VIVO | | |
| 5 mice per group | | |
| Non-treated infected control | 301.2 | 0.0 |
| Zearalane 1000 μg in 1% squalene | 74.2 | 75.4 |
| Zearalane 750 μg in 1% squalene | 111.6 | 62.9 |
| Zearalane 500 μg in 1% squalene | 144.4 | 52.1 |
| Zearalane 250 μg in 1% squalene | 168.8 | 44.0 |
| Zearalane 100 μg in 1% squalene | 192.6 | 36.1 |
| Zearalane 500 μg in HBSS* | 149.0 | 50.5 |
| squalene - 1% | 266.2 | 11.6 |
| Levamisole-positive control | 45.2 | 85.0 |
| Dideoxyzearalane 1000 μg in HBSS | 250.2 | 16.9 |
| IN VITRO** | | |
| 3 mice per group | | |
| N. brasiliensis | 291.0 | 0.0 |
| N. brasiliensis in squalene (1 ml-per dish) | 225.3 | 0.0 |
| Zearalane 4000 μg/ml in HBSS | 69.3 | 69.2 |
| Zearalane 2000 μg/ml in HBSS | 86.7 | 61.5 |
| Zearalane 400 μg/ml in HBSS | 107.0 | 52.5 |
| Zearalane 400 μg/ml in Squalene | 133.7 | 40.7 |
| Zearalane 40 μg/ml in HBSS | 112.0 | 50.3 |
| Levamisole 12 μg/ml (+ control) | 28.3 | 87.4 |
| Squalene 1% (1 ml per dish) | 211.7 | 6.0 |
| HBSS (1 ml-per dish) | 210.0 | 6.8 |
| 4-Deoxy-Zearalanol 1000 μg in HBSS | 124.7 | 44.7 |

TABLE 2-continued

Efficacy Study of Anthelmintic Compounds vs.
Nippostrongylus brasiliensis in Mice

| Treatment | Mean # of Nematodes | Percent Efficacy |
|---|---|---|
| Dideoxyzearalane 1000 μg in HBSS | 152.7 | 32.2 |

*HBSS is Hank's Balanced Salt Solution
**In Vitro studies were conducted as follows: The larvae of N. Brasiliensis were allowed to stand in the petri dishes containing respective treatments for 4 hours. The contents (larvae and respective treatments for 4 hours. The contents (larvae compounds) were then aspirated into a tuberculin syringe and injected s.c. into mice belonging to the respective treatment groups.

TABLE 3

Efficacy Study of Anthelmintic Compounds vs.
Nippostrongylus brasiliensis in Mice

| | Treatment & Groups 5 mice/group | Mean # of Nematodes | Percent Efficacy |
|---|---|---|---|
| 1. | Non-treated infected control (HBSS)* Day −6 | 196.8 | 0.0 |
| 2. | Levamisole - positive control Day −6 | 64.8 | 67.1 |
| 3. | Zearalane 500 μg Day −6 | 123.8 | 37.1 |
| 4. | Non-treated infected control (HBSS) Day −3 | 202.0 | 0.0 |
| 5. | Levamisole-positive control Day −3 | 63.8 | 68.4 |
| 6. | Zearalane 500 μg Day −3 | 117.0 | 42.1 |
| 7. | Non-treated infected control (HBSS) Day −1 | 203.8 | 0.0 |
| 8. | Levamisole-positive control Day −1 | 41.4 | 79.7 |
| 9. | Zearalane 500 μg Day −1 | 105.4 | 48.3 |
| 10. | Non-treated infected control (HBSS) Day +1 | 202.8 | 0.0 |
| 11. | Levamisole-positive control Day +1 | 49.0 | 75.8 |
| 12. | Zearalane 500 μg Day +1 | 103.8 | 48.8 |
| 13. | Non-treated infected control (HBSS) Day +3 | 199.2 | 0.0 |
| 14. | Levamisole-positive control Day +3 | 35.2 | 82.3 |
| 15. | Zearalane 500 μg Day +3 | 108.0 | 45.8 |
| 16. | Non-treated infected control (HBSS) Day +6 | 210.0 | 0.0 |
| 17. | Levamisole-positive control Day +6 | 57.0 | 72.9 |
| 18. | Zearalane 500 μg Day +6 | 113.2 | 46.1 |

*HBSS is Hank's Balanced Salt Solution

What is claimd is:

1. A method for controlling helmintic parasites in an animal suffering from helmintic parasitic infections, comprising;
   administering to said animal a helmintic parasite controlling amount of at least one compound selected from the group consisting of zearalenone, zearalanone, zearalene, zearalane, zearalenol, zearalanol, and dideoxyzearalane.

2. The method of claim 1 wherein said compound is selected from the group consisting of zearalane and zearalanol.

3. The method of claim 1 wherein said compound is administered in an amount from about 1–20 mg/kg of body weight.

4. The method of claim 1 wherein said compound is administered orally.

5. The method of claim 4 wherein said oral method is selected from the group consisting of administering said compound to said animals in tablets, suspensions, solutions, boluses, emulsions, capsules, powders, syrups, drinking water compositions, or feed compositions.

6. The method of claim 5 wherein said compound is administered in a feed composition, said feed composition further comprising:
   a nutritionally balanced feed; and
   an helmintic parasite controlling amount of at least one of said compounds admixed with said feed.

7. The method of claim 1 wherein said compound is administered by injecting a formulation, said formulation further comprising:
   a biocompatible and said compound compatible vehicle; and
   an helmintic parasite controlling amount of at least one of said compounds admixed with said vehicle.

8. The method of claim 7 wherein said vehicle is selected from the group consisting of carboxymethylcellulose (CMC), squalene, and Hank's Balanced Salt Solution.

9. The method of claim 1 wherein said compound is administered using an implant, said implant further comprising:
   a biocompatible and said compound compatible implant material; and
   an helmintic parasite controlling amount of at least one of said compounds admixed with said implant material.

10. The method of claim 1 wherein said helmintic parasites are selected from the group consisting of trematodes, cestodes, and nematodes.

11. The method of claim 1 wherein said helmintic parasites are selected from the group consisting of helmintic parasites that infect said animal's respiratory and gastro-intestinal tract.

12. The method of claim 1 wherein said helmintic parasites are selected from the group consisting of lungworms, roundworms, tapeworms, ringworms, pinworms, and hookworms.

13. The method of claim 1 wherein said animals are selected from the group of animal species consisting of human, bovine, porcine, canine, feline, equine, avian, and ovine.

14. The method of claim 13 wherein said animals are selected from the group consisting of cattle, swine, sheep, chickens, and turkeys.

* * * * *

UNITED STATES PATENT AND TRADEMARK OFFICE
CERTIFICATE OF CORRECTION

PATENT NO. : 4,778,821
DATED : October 18, 1988
INVENTOR(S) : Ellen R. Clough et al It is certified that error appears in the above-identified patent and that said Letters Patent is hereby corrected as shown below:

Column 1, line 32, "piparazines" should read --piperazines--

Column 1, line 55, "acaracidal" should read --acaricidal--

Column 3, line 19, "reucing" should read --reducing--

Column 4, line 58, "biocompatable" should read --biocompatible--

Column 8, line 57, "appaarance" should read --appearance--

Column 8, line 62, "extendig" should read --extending--

Column 9, Table 1, In the Heading, Following "Treatment" insert --*--

Column 10, Table 2, lines 9-10, In the Footnote **, delete the second sentence --The contents (larvae and respective treatments for 4 hours.--

Column 10, line 52, "claimd" should read --claimed--

Signed and Sealed this

Seventeenth Day of October, 1989

Attest:

DONALD J. QUIGG

Attesting Officer

Commissioner of Patents and Trademarks